US010058536B2

(12) United States Patent
Takae et al.

(10) Patent No.: US 10,058,536 B2
(45) Date of Patent: Aug. 28, 2018

(54) PHARMACEUTICAL COMPOSITION CONTAINING MIRABEGRON

(71) Applicant: ASTELLAS PHARMA INC., Tokyo (JP)

(72) Inventors: Seiji Takae, Tokyo (JP); Toshiro Sakai, Tokyo (JP); Yuki Kasashima, Tokyo (JP); Yurina Ansei, Tokyo (JP); Tsuyoshi Kiyota, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 15/553,107

(22) PCT Filed: Mar. 31, 2016

(86) PCT No.: PCT/JP2016/060745
§ 371 (c)(1),
(2) Date: Aug. 23, 2017

(87) PCT Pub. No.: WO2016/159267
PCT Pub. Date: Oct. 6, 2016

(65) Prior Publication Data
US 2018/0036288 A1  Feb. 8, 2018

(30) Foreign Application Priority Data

Mar. 31, 2015  (JP) .................................. 2015-073911

(51) Int. Cl.
A61K 9/50 (2006.01)
A61K 31/425 (2006.01)
(Continued)

(52) U.S. Cl.
CPC .............. A61K 31/426 (2013.01); A61K 9/10 (2013.01); A61K 31/167 (2013.01); A61K 47/12 (2013.01);
(Continued)

(58) Field of Classification Search
CPC .. A61K 9/1635; A61K 9/1632; A61K 9/1605; A61K 31/425
(Continued)

(56) References Cited

U.S. PATENT DOCUMENTS 6,346,532 B1   2/2002   Maruyama et al.
6,514,492 B1*  2/2003   Gao ..................... A61K 9/0095
                                                424/400
(Continued)

FOREIGN PATENT DOCUMENTS

CN        1879610 A    12/2006
JP        8-259410 A   10/1996
(Continued)

OTHER PUBLICATIONS

CN1879610, English translation. 2006.*
(Continued)

Primary Examiner — Shengjun Wang
(74) Attorney, Agent, or Firm — Kilpatrick Townsend & Stockton LLP

(57) ABSTRACT

To provide: (1) a modified release liquid (suspension) containing mirabegron, (2) a ready-to-suspend pharmaceutical composition containing mirabegron, and (3) a mirabegron-containing pharmaceutical composition that does not generate undissolved lumps, even when it is suspended at the time of use. The present invention relates to a pharmaceutical composition containing a complex of mirabegron or a pharmaceutically acceptable salt thereof with sodium polystyrene sulfonate.

9 Claims, 2 Drawing Sheets

(51) Int. Cl.
    *A61K 31/426*    (2006.01)
    *A61K 31/167*    (2006.01)
    *A61K 47/12*     (2006.01)
    *A61K 9/10*      (2006.01)
    *A61K 47/36*     (2006.01)
    *A61K 47/50*     (2017.01)
    *A61K 47/32*     (2006.01)

(52) U.S. Cl.
    CPC .............. *A61K 47/32* (2013.01); *A61K 47/36* (2013.01); *A61K 47/50* (2017.08)

(58) Field of Classification Search
    USPC .......................... 424/497, 496, 400; 514/370
    See application file for complete search history.

(56) References Cited

U.S. PATENT DOCUMENTS

| | | |
|---|---|---|
| 2002/0164373 A1 | 11/2002 | Maloney |
| 2005/0004190 A1 | 1/2005 | Kawazoe et al. |
| 2006/0115540 A1 | 6/2006 | Takasu et al. |
| 2010/0144807 A1 | 6/2010 | Takaishi et al. |
| 2010/0255146 A1 | 10/2010 | Seko et al. |
| 2015/0031734 A1 | 1/2015 | Kasashima et al. |

FOREIGN PATENT DOCUMENTS

| | | |
|---|---|---|
| JP | 2003-104912 A | 4/2003 |
| JP | 2003-522127 A | 7/2003 |
| JP | 2005-304378 A | 11/2005 |
| JP | 3930897 | 3/2007 |
| WO | 1999/20607 | 4/1999 |
| WO | 2003/037881 A1 | 5/2003 |
| WO | 2004/041276 A1 | 5/2004 |
| WO | 2010/038690 | 8/2010 |
| WO | 2013/147134 A1 | 10/2013 |

OTHER PUBLICATIONS

Iyakuhin Tenkabutsu Jiten; Jul. 2007, p. 272, left column.
International Search Report; PCT/JP2016/060745 dated Jun. 24, 2016.

* cited by examiner

PHARMACEUTICAL COMPOSITION CONTAINING MIRABEGRON

CROSS-REFERENCE TO RELATED APPLICATIONS

This application is a National Phase application under 35 USC § 371 of Application No. PCT/JP2016/060745, filed Mar. 31, 2016, which application claims priority to Japanese Patent Application No. 2015-073911, filed Mar. 31, 2015, the teachings of all of which are hereby incorporated by reference in their entireties for all purposes.

TECHNICAL FIELD

The present invention relates to a pharmaceutical composition comprising mirabegron. More particularly, the present invention relates to a pharmaceutical composition comprising a complex of mirabegron or a pharmaceutically acceptable salt thereof with sodium polystyrene sulfonate.

BACKGROUND ART

Mirabegron has the following chemical structural formula:

[Chem. 1]

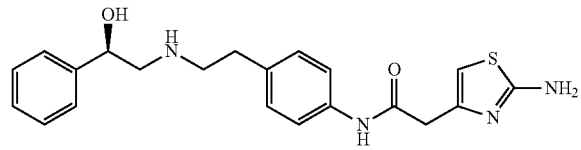

Mirabegron or a pharmaceutically acceptable salt thereof has a β3-adrenergic receptor agonist activity, and is known to be useful as a therapeutic agent for overactive bladder (Patent literatures 1 to 3). Tablets containing mirabegron have already been placed on the market, and are sold in Japan, as "Betanis (registered trademark) tablet 25 mg" and "Betanis (registered trademark) tablet 50 mg".

It is known that the pharmacokinetics vary depending on the presence or absence of food intake in clinical studies conducted in the development phase of the mirabegron (Patent literature 4). When the pharmacokinetics vary depending on the presence or absence of food intake, inevitably, it affects its effects. Particularly in medicine, if an effect different from the prediction occurs, since it is considered that it may lead to unexpected situations, it is necessary to predict certain effects. Therefore, the development of a drug in which a variation in pharmacokinetics depending on the presence or absence of food intake is minimized is strongly demanded. It is known that the variation in pharmacokinetics depending on the presence or absence of food intake in mirabegron can be reduced by controlling the drug release using various additives (Patent literature 4).

The formulations that are currently placed on the market are tablets, and thus, development of various dosage forms, such as liquids and solutions or the like, is desired from the viewpoint of a patient's further drug dosing compliance, or the like.

As a modified release liquid, a pharmaceutical composition, such as granules (suspension) or the like, containing an alkyl sulfate of mirabegron, is known (Patent literature 5).

On the other hand, in the medical field, for example, a ready-to-suspend preparation is prepared in medical facilities, and it is brought back to a general household, and taken in accordance with dosage and administration. When a ready-to-suspend preparation is prepared in medical facilities, it is desirable that a suspension in which a thickener (for example, xanthan gum) is dissolved is prepared within an appropriate time. When the preparation is brought back to a household and taken, since the suspension is resuspended before medication, and a predetermined dose is divided, it is desirable to maintain the suspended state for an appropriate period of time.

When a ready-to-suspend preparation is suspended in a solvent, such as water, a thickener tends to be in a lumpy state, and since a thickener in the lumpy state is incompletely hydrated, the thickener may not be able to fully demonstrate its function.

For example, as a method of preventing xanthan gum from being in a lumpy state, in order to improve the development of viscosity and enhance solubility when xanthan gum is dissolved, an invention relating to a composition, wherein metal salts are bound to the surface of xanthan gum, and as a result, the dissolution of the surface is controlled by modifying the surface of xanthan gum, and the dispersion properties of xanthan gum in water are improved, is proposed (Patent literature 6).

In order to provide a viscous liquid, without forming undissolved lumps of powder, even at ordinary temperature, an invention relating to a powdery administration-assisting food containing an anionic polymer and a preventive agent of undissolved lumps of powder, such as sodium hydrogen carbonate or the like, is proposed (Patent literature 7).

A powdery composition containing a gelling agent for preparing sol-like or gel-like food, characterized by containing water-insoluble calcium-containing material powder, which functions as a preventive agent of undissolved lumps of flour, is disclosed (Patent literature 8).

However, Patent literatures 6 to 8 do not disclose mirabegron or a pharmaceutically acceptable salt thereof. Additionally, Patent literatures 6 to 8 disclose inventions relating to food, but do not disclose any inventions relating to medicaments.

Therefore, there is still room for improvement in providing a pharmaceutical composition containing mirabegron or a pharmaceutically acceptable salt thereof which does not generate undissolved lumps, even when a ready-to-suspend preparation is prepared using a solvent, such as water or the like.

CITATION LIST

Patent Literature

[Patent literature 1] WO 2004/041276
[Patent literature 2] WO 99/20607
[Patent literature 3] WO 03/037881
[Patent literature 4] WO 2010/038690
[Patent literature 5] WO 2013/147134
[Patent literature 6] Japanese Patent No. 3930897
[Patent literature 7] Japanese Unexamined Patent Publication (Kokai) No. 2003-104912
[Patent literature 8] Japanese Unexamined Patent Publication (Kokai) No. 2005-304378

SUMMARY OF INVENTION

Technical Problem

With respect to a ready-to-suspend pharmaceutical composition, since it is mixed with a solvent in the medical field or at home, there is a concern to form undissolved lumps depending on a shaking method. Because there is a possibility that a suspension in which undissolved lumps are formed may affect not only the easiness of taking but also its drug efficacy, a composition capable of dispersing a pharmaceutical composition with simple shaking, without using a special instrument, is desired.

Therefore, the objects of the present invention are:
(1) to provide a modified release liquid (suspension) containing mirabegron,
(2) to provide a ready-to-suspend pharmaceutical composition containing mirabegron, and
(3) to provide a mirabegron-containing pharmaceutical composition that does not generate undissolved lumps, even when it is suspended at the time of use.

Solution to Problem

The present inventors focused attention on the improvement of the generation of undissolved lumps when suspended at the time of use, conducted intensive studies, and completed the present invention.

The present invention provides:
[1] a pharmaceutical composition comprising a complex of mirabegron or a pharmaceutically acceptable salt thereof with sodium polystyrene sulfonate,
[2] the pharmaceutical composition of [1], further comprising a thickener and a hydrophobic substance,
[3] the pharmaceutical composition of [2], wherein the hydrophobic substance is one member or two or more members selected from the group consisting of a higher fatty acid or a metal salt thereof, and an inorganic substance,
[4] the pharmaceutical composition of [2] or [3], wherein the hydrophobic substance is magnesium stearate and/or calcium stearate,
[5] the pharmaceutical composition of any one of [2] to [4], wherein the content of the hydrophobic substance is 0.5% by weight to 35% by weight with respect to the weight of the thickener,
[6] the pharmaceutical composition of any one of [2] to [5], wherein the thickener is one member or two or more members selected from the group consisting of xanthan gum, guar gum, locust bean gum, gellan gum, carboxymethyl cellulose sodium, gelatin, hydroxyethyl cellulose, hydroxypropyl cellulose, carrageenan, methylcellulose, sodium alginate, hypromellose, and polyvinyl alcohol,
[7] the pharmaceutical composition of any one of [2] to [6], wherein the thickener is xanthan gum,
[8] the pharmaceutical composition of any one of [2] to [7], wherein the content of the thickener is 1% by weight to 70% by weight with respect to the weight of the pharmaceutical composition,
[9] the pharmaceutical composition of any one of [1] to [8], wherein the pharmaceutical composition is a ready-to-suspend pharmaceutical composition,
[10] the pharmaceutical composition of any one of [1] to [9], wherein the pharmaceutical composition is a pharmaceutical composition for oral administration,
[11] the pharmaceutical composition of any one of [1] to [10], wherein the pharmaceutical composition is a pharmaceutical composition for treating one member or two or more members selected from the group consisting of urinary urgency, urinary frequency, urge urinary incontinence, and neuropathic detrusor overactivity, which are associated with overactive bladder,
[12] a method of preventing undissolved lumps from being formed, when a ready-to-suspend preparation is prepared, by using a hydrophobic substance in the pharmaceutical composition containing a complex of mirabegron or a pharmaceutically acceptable salt thereof with sodium polystyrene sulfonate, and a thickener,
[13] a use of a hydrophobic substance for preventing undissolved lumps from being formed in the preparation of a pharmaceutical composition containing a complex of mirabegron or a pharmaceutically acceptable salt thereof with sodium polystyrene sulfonate, and a thickener, and
[14] the pharmaceutical composition of any one of [1] to [11], wherein sodium polystyrene sulfonate is Amberlite (registered trademark) IRP69.

Advantageous Effects of Invention

According to the pharmaceutical composition of the present invention, a modified release liquid (suspension) containing mirabegron can be provided, and by rendering mirabegron a modified release liquid (suspension), it can be taken for a patient who needs a dose adjustment, such as a child, and drug dosing compliance is improved. According to the pharmaceutical composition of the present invention, the pharmaceutical composition can be dispersed with simple shaking, without using a special instrument when suspended at the time of use, and the generation of undissolved lumps can be inhibited.

DESCRIPTION OF EMBODIMENTS

Figure 1:
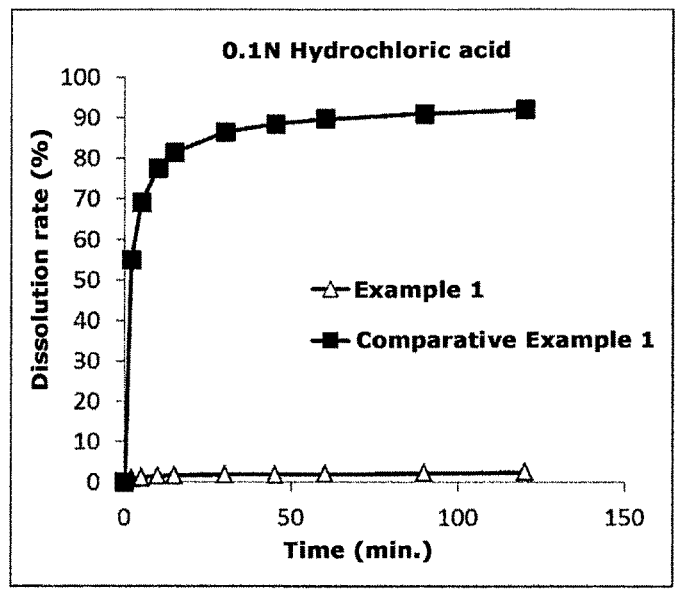
FIG. 1 is a graph showing the dissolution profiles of the suspensions of Example 1 and Comparative Example 1 in 0.1 N hydrochloric acid.
Figure 2:
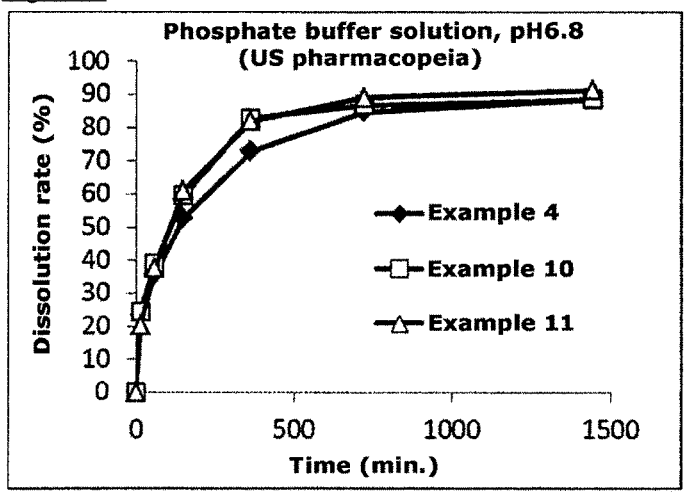
FIG. 2 is a graph showing the dissolution profiles of the suspensions of Examples 4, 10, and 11 in a phosphate buffer solution, pH 6.8 (US pharmacopeia).
Figure 3:
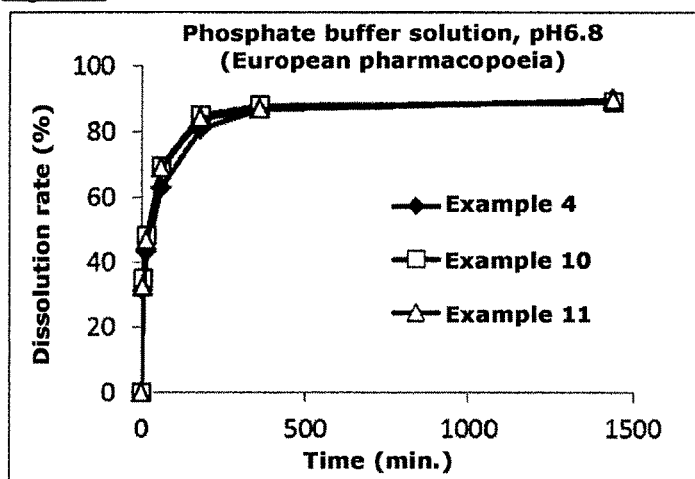
FIG. 3 is a graph showing the dissolution profiles of the suspensions of Examples 4, 10, and 11 in a phosphate buffer solution, pH 6.8 (European pharmacopoeia).
Figure 4:
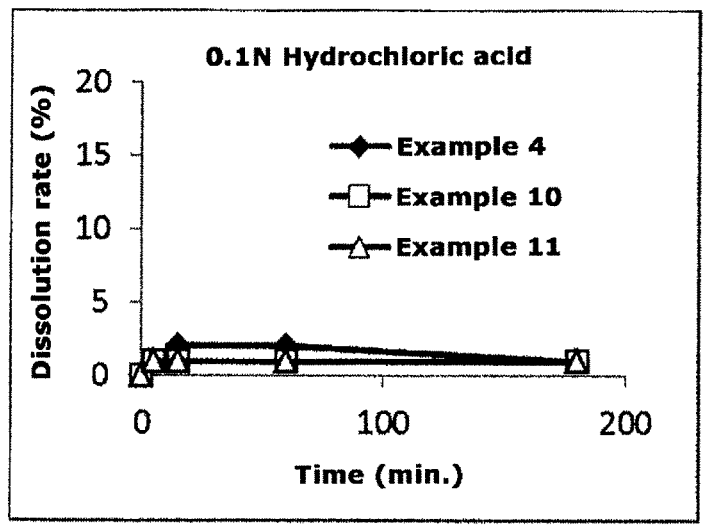
FIG. 4 is a graph showing the dissolution profiles of the suspensions of Examples 4, 10, and 11 in 0.1 N hydrochloric acid.
Figure 5:
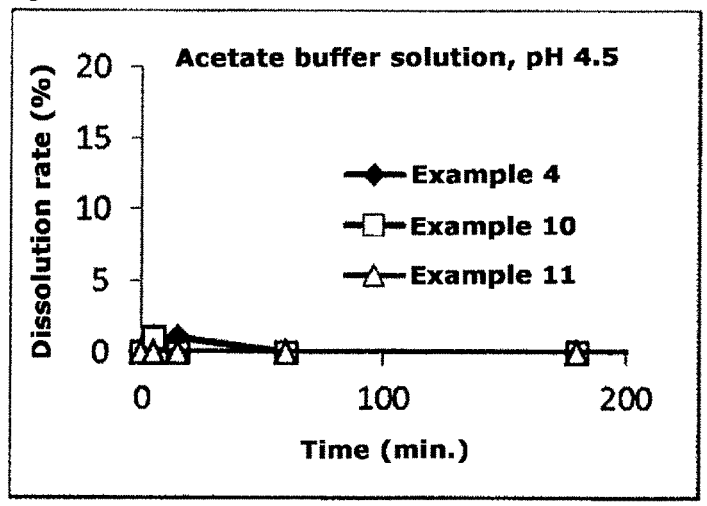
FIG. 5 is a graph showing the dissolution profiles of the suspensions of Examples 4, 10, and 11 in an acetate buffer solution, pH 4.5.
Figure 6:
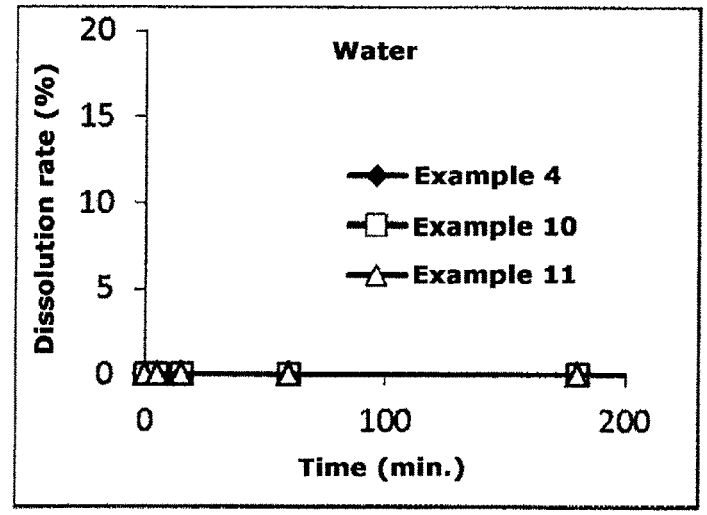
FIG. 6 is a graph showing the dissolution profiles of the suspensions of Examples 4, 10, and 11 in water.

Embodiments of the present invention will be explained in detail hereinafter.

The term "suspended at the time of use" as used herein means a state where the complex contained in the pharmaceutical composition of the present invention before taking is dispersed or suspended in a solvent, such as water or the like.

The term "undissolved lumps" as used herein means a state where a thickener or the like is not partially dissolved or dispersed when suspended at the time of use, and as a result, a specific number or more of undissolved particles or remaining particles (also called lumps) are present. For example, when a suspension is prepared under the conditions as described in Experimental Examples 4, 5, and 8 below, it is defined as a state where a specific number or more of lumps larger than 2800 μm are present in an embodiment, and a state where a specific number or more of lumps between 1400 µm and 2800 µm are present in another embodiment.

The term "sedimentation stability" as used herein means a property in which sedimentation is not confirmed after being suspended at the time of use, and the suspended state is maintained. For example, it can be evaluated by (1) a method described in Experimental Example 4 below, i.e., a method of 20 reciprocal shaking for 10 seconds at a distance of 20 cm, (2) a method described in Experimental Example 5 below, i.e., a method of 50 reciprocal shaking for 10 seconds at a distance of 20 cm, followed by 100 reciprocal shaking for 50 seconds, (3) a method of 120 reciprocal shaking for 60 seconds at a distance of 20 cm, or (4) a method of 50 reciprocal shaking for 10 seconds at a distance of 20 cm. As evaluation criteria, it means that, when a test sample is allowed to stand after the shaking, no sedimentation is observed for 6 hours in an embodiment, and for 12 hours in an embodiment.

The pharmaceutical composition of the present invention will be explained in detail hereinafter.

Mirabegron or a pharmaceutically acceptable salt thereof, which is used in the present invention, is easily available, for example, by a method described in Patent literature 2, or in the same manner as that.

Mirabegron may be in a free form which is not a salt in an embodiment, and may form a pharmaceutically acceptable salt with an acid in other embodiments. Examples of such a salt include an acid addition salt with an inorganic acid, such as hydrochloric acid, hydrobromic acid, hydroiodic acid, sulfuric acid, nitric acid, phosphoric acid, or the like; and an acid addition salt with an organic acid, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid, or the like. These salts can be prepared by conventional methods.

The dose of mirabegron or a pharmaceutically acceptable salt thereof may be appropriately determined for each patient in accordance with the symptoms, the age and the sex of a patient to be treated, and the like. When mirabegron is orally administered to an adult, the daily dose is 1 mg to 200 mg (converted as the free form), and is administered once or divided into two to four doses per day.

The content of mirabegron or a pharmaceutically acceptable salt thereof with respect to the weight of the pharmaceutical composition is, for example, 1% by weight to 70% by weight in an embodiment, 5% by weight to 70% by weight in an embodiment, and 5% by weight to 50% by weight in an embodiment. The concentration of mirabegron or a pharmaceutically acceptable salt thereof when suspended at the time of use is 0.2 mg/mL to 20 mg/mL in an embodiment, 0.4 mg/mL to 15 mg/mL in an embodiment, and 1 mg/mL to 10 mg/mL in an embodiment.

Sodium polystyrene sulfonate, which is used in the present invention, is a cation exchange resin, which forms a strongly acidic salt. Examples of sodium polystyrene sulfonate include Amberlite (registered trademark) IRP69 (The Dow Chemical Company), Purolite (registered trademark) C100MRNS (Purolite Ltd.), Purolite (registered trademark) NaResNS (Purolite Ltd.), Sodium polystyrene sulfonate USP, and the like. Amberlite (registered trademark) IRP69 is preferable.

The content of sodium polystyrene sulfonate is not particularly limited, so long as it can control the release rate of the drug, to the extent that the blood concentration profile of the drug is not affected by the presence or absence of food intake, by forming a complex with mirabegron or a pharmaceutically acceptable salt thereof.

The content ratio of sodium polystyrene sulfonate is not particularly limited, so long as it forms a complex with mirabegron or a pharmaceutically acceptable salt thereof, and can control the release rate of mirabegron. More particularly, the content ratio of mirabegron or a pharmaceutically acceptable salt thereof to sodium polystyrene sulfonate (mirabegron or a pharmaceutically acceptable salt thereof: sodium polystyrene sulfonate, as a weight ratio) is, for example, 1:0.5 to 1:20 in an embodiment, 1:1 to 1:10 in an embodiment, 1:1 to 1:5 in an embodiment, and 1:2 to 1:3 in an embodiment. The content ratio of mirabegron to sodium polystyrene sulfonate, as a weight ratio, is 1:0.5 to 1:20 in an embodiment, 1:1 to 1:10 in an embodiment, 1:1 to 1:5 in an embodiment, and 1:2 to 1:3 in an embodiment. The concentration of mirabegron or a pharmaceutically acceptable salt thereof when suspended at the time of use is 0.1 mg/mL to 400 mg/mL in an embodiment, 0.4 mg/mL to 150 mg/mL in an embodiment, and 1 mg/mL to 50 mg/mL in an embodiment.

The complex liquid of mirabegron or a pharmaceutically acceptable salt thereof and sodium polystyrene sulfonate has preferably a pH of 8 or less.

The complex of mirabegron or a pharmaceutically acceptable salt thereof with sodium polystyrene sulfonate in the present invention means a complex comprising at least mirabegron or a pharmaceutically acceptable salt thereof and sodium polystyrene sulfonate in an embodiment, a complex consisting of mirabegron or a pharmaceutically acceptable salt thereof and sodium polystyrene sulfonate in an embodiment, and a complex of a cation of protonated mirabegron with a polystyrene sulfonate anion in an embodiment.

The thickener, which is used in the present invention, is not particularly limited, so long as the complex of mirabegron or a pharmaceutically acceptable salt thereof with sodium polystyrene sulfonate can be dispersed, when suspended at the time of use. Examples of the thickener include xanthan gum, guar gum, locust bean gum, gellan gum, carboxymethyl cellulose sodium, gelatin, hydroxyethyl cellulose, hydroxypropyl cellulose, carrageenan, methylcellulose, sodium alginate, hypromellose, and polyvinyl alcohol, and a mixture of these compounds, and the like.

A preferred thickener used in the present invention is xanthan gum. Examples of xanthan gum include Xantural 11K (CP Kelco), Xantural 180 (CP Kelco), and the like. Only one type of xanthan gum may be used, or two or more types of different grades of xanthan gum may be appropriately combined and used. xanthan gum that is classified using a sieve, or xanthan gum that is pulverized using a pulverizer may be used.

The content of the thickener is not particularly limited, so long as the complex of mirabegron or a pharmaceutically acceptable salt thereof with sodium polystyrene sulfonate can be dispersed, when suspended at the time of use. The content of the thickener with respect to the weight of the pharmaceutical composition is, for example, 1% by weight to 70% by weight in an embodiment, 1% by weight to 50% by weight in an embodiment, 1% by weight to 20% by weight in an embodiment, and 1% by weight to 5% by weight in an embodiment. The content of the thickener with respect to the weight of the suspension (suspension liquid) when suspended at the time of use is 0.1% by weight to 2% by weight in an embodiment, 0.15% by weight to 1% by weight in an embodiment, and 0.2% by weight to 0.5% by weight in an embodiment.

The hydrophobic substance, which is used in the present invention, is not particularly limited, so long as it can inhibit the generation of undissolved lumps when a solvent, such as water or the like, is added to the composition containing the thickener. The hydrophobic substance is not particularly limited, so long as it is one member or two or more members selected from the group consisting of a higher fatty acid or a metal salt thereof, and an inorganic substance.

Examples of the hydrophobic substance, which is used in the present invention, include magnesium stearate, calcium stearate, talc, calcium carbonate, stearic acid, and the like. A preferred hydrophobic substance is a substance in which, when a cylindrical tablet (diameter: 7 mm, thickness: 2.8 mm) containing the hydrophobic substance is prepared, a contact angle of the tablet to water is 80° or more. The contact angle to water as used herein means, in the case where a tablet containing the hydrophobic substance is prepared, an angle when a dropped water droplet is brought into contact with the surface of the tablet. For example, 2 μL of a water droplet is formed at the tip of a needle (spec), and the contact angle is measured using a contact angle measuring apparatus (DM-501, Kyowa Interface Science Co., Ltd.) after 100 msec. from the drop of the droplet on the surface of the tablet. In general, the contact angle can be calculated by the measurement at room temperature. More particularly, magnesium stearate or calcium stearate may be used. Examples of magnesium stearate include Parteck (registered trademark) LUB MST (Product name, Merck & Co., Inc.) and the like. Examples of calcium stearate include Parteck (registered trademark) LUB CST (Product name, Merck & Co., Inc.) and the like.

The content of the hydrophobic substance is not particularly limited, so long as it can inhibit the generation of undissolved lumps when a solvent, such as water or the like, is added to the composition containing the thickener. The content of the hydrophobic substance with respect to the weight of the pharmaceutical composition is, for example, 0.1% by weight to 10% by weight in an embodiment, 0.5% by weight to 5% by weight in an embodiment, and 1% by weight to 3% by weight in an embodiment.

The content of the hydrophobic substance with respect to the weight of the thickener is 0.5% by weight to 50% by weight in an embodiment, 2% by weight to 40% by weight in an embodiment, and 5% by weight to 35% by weight in an embodiment.

The viscosity of the suspension is not particularly limited, for example, so long as the complex of the drug with sodium polystyrene sulfonate is uniformly dispersed, and the dispersion stability is improved. More particularly, for example, when the viscosity is measured at 25° C. and at a paddle rotation speed of 100 rpm, using a rotational viscometer (Brookfield digital viscometer, Model: RVDV-II+ PRO), the viscosity is 25 mPa·s to 8000 mPa·s in an embodiment, 50 mPa·s to 5000 mPa·s in an embodiment, and 50 mPa·s to 200 mPa·s in an embodiment.

Various pharmaceutical additives may be appropriately used to prepare the pharmaceutical composition of the present invention, if desired, and are not particularly limited, so long as they are pharmaceutically and pharmacologically acceptable. Examples of the pharmaceutical additives include a filler, a binder, a preservative, a corrigent, a flavor, a humectant, a buffering agent, a pH adjuster, an antifoaming agent, a solvent, and the like.

Examples of the filler include lactose, sucrose, D-mannitol, D-sorbitol, crystalline cellulose, and the like.

Examples of the binder include gum arabic, hypromellose, hydroxypropyl cellulose, hydroxyethyl cellulose, and the like.

Examples of the preservative include sodium benzoate, methyl parahydroxybenzoate, ethyl parahydroxybenzoate, propyl parahydroxybenzoate, butyl parahydroxybenzoate, benzoic acid, benzyl alcohol, sorbic acid, acetic acid, and salts thereof.

Examples of the corrigent include sugars and sugar alcohols (such as sucrose, fructose, lactose, sorbitol, mannitol, xylitol, erythritol, trehalose, and the like), and sweeteners (such as aspartame, acesulfame potassium, sucralose, neotame, saccharin, and the like).

Examples of the flavor include lemon, lemon lime, orange, menthol, strawberry, banana, raspberry, bubble gum flavor, and the like.

Examples of the humectant include polyoxyethylene sorbitan fatty acid esters, such as polysorbate 80 and arasel 83, polyoxyethylene hydrogenated castor oil, such as HCO-50, a surfactant, such as sugar ester, and the like.

Examples of the buffering agent include citric acid, phosphoric acid, boric acid, acetic acid, succinic acid, fumaric acid, tartaric acid, ascorbic acid or salts thereof, glutamic acid, glutamine, glycine, aspartic acid, alanine, arginine or salts thereof, magnesium oxide, zinc oxide, magnesium hydroxide or salts thereof, and the like.

Examples of the pH adjuster include, in addition to alkaline agents, acids, such as citric acid, acetic acid, hydrochloric acid, succinic acid, tartaric acid, malic acid, phosphoric acid, boric acid, fumaric acid, ascorbic acid, glutamic acid, and the like.

Examples of the antifoaming agent include simethicone, dimethicone, light anhydrous silicic acid, and the like.

Examples of the solvent include glycerin, propylene glycol, and the like.

In addition to these pharmaceutical additives, a nonionic substance may be added, if necessary.

These pharmaceutical additives may be used alone, or as an appropriate combination of two or more types.

A method of producing the pharmaceutical composition of the present invention will be explained hereinafter.

The production method of the present invention comprises, for example, (1) a complex formation step, (2) a solvent removal step, and (3) a granulation and mixing step.

(1) Complex Formation Step:

As a preparation step for complex formation, a complex liquid is prepared, for example, by mixing and stirring sodium polystyrene sulfonate, mirabegron pulverized using, for example, comil or the like, and a solvent. Examples of the solvent include water, a pH adjustment agent, or an optionally water-soluble organic solvent. The temperature during the reaction is not particularly limited, but the reaction is preferably carried out at 30° C. to 70° C. The reaction time is about 1 to 24 hours. By the reaction, a complex of the drug and sodium polystyrene sulfonate, in which the drug is adsorbed at 80% or more of the theoretical amount of ion adsorption, can be quantitatively obtained. Preferably, a complex of the drug and sodium polystyrene sulfonate, in which 85% to 100% of the drug is adsorbed, can be obtained. In connection with this, raw materials may be pulverized using, for example, a pin mill or the like, before use.

(2) Solvent Removal Step:

In this step, the solvent of the complex liquid is evaporated using, for example, a spray dryer, a fluidized bed granulator, filtration, or the like, to obtain the complex.

(3) Granulation and Mixing Step:

In this step, for example, the complex, a thickener, and various pharmaceutical additives are mixed, and granulated with a binder solution. The granulated product is mixed with a hydrophobic substance.

The pharmaceutical additives may be added in any step.

The pharmaceutical composition of the present invention includes the granulated product of (3) per se. Alternatively, the granulated product obtained in (3) may be used by a method known per se, as a formulation, such as granules, powders, dry syrups, pills, capsules, tablets, or the like, or as a ready-to-suspend preparation, in which these dosage forms are suspended in a solvent before taking.

The pharmaceutical composition of the present invention is used as a pharmaceutical composition for treating, for example, urinary urgency, urinary frequency, urge urinary incontinence, neuropathic detrusor overactivity, or the like, which are associated with overactive bladder.

The method of producing the pharmaceutical composition of the present invention includes a production method in which the above-mentioned production method is appropriately combined with a method known per se.

The present invention includes a method of preventing undissolved lumps from being formed, when a ready-to-suspend preparation is prepared, by using a hydrophobic substance in the pharmaceutical composition containing a complex of mirabegron or a pharmaceutically acceptable salt thereof with sodium polystyrene sulfonate, and a thickener.

With respect to the "complex of mirabegron or a pharmaceutically acceptable salt thereof with sodium polystyrene sulfonate" and the "hydrophobic substance", which are used in the method of preventing undissolved lumps from being formed of the present invention, the explanations for the pharmaceutical composition of the present invention can be directly applied.

In the method of preventing undissolved lumps from being formed of the present invention, the generation of undissolved lumps due to the thickener can be inhibited, by adding the hydrophobic substance, when the pharmaceutical composition containing the complex of mirabegron or a pharmaceutically acceptable salt thereof with sodium polystyrene sulfonate is prepared.

With respect to the content, the method of addition, or the like, of each component in the method of preventing undissolved lumps from being formed of the present invention, the explanations for the pharmaceutical composition of the present invention and its production method can be directly applied.

The present invention includes a use of a hydrophobic substance for preventing undissolved lumps from being formed in the preparation of a pharmaceutical composition containing a complex of mirabegron or a pharmaceutically acceptable salt thereof with sodium polystyrene sulfonate, and a thickener.

With respect to the "pharmaceutical composition containing a complex of mirabegron or a pharmaceutically acceptable salt thereof with sodium polystyrene sulfonate" and the "hydrophobic substance", which are used in the use of a hydrophobic substance of the present invention, the explanations for the pharmaceutical composition of the present invention can be directly applied.

According to the use of a hydrophobic substance of the present invention, in the supply of the pharmaceutical composition containing a complex of mirabegron or a pharmaceutically acceptable salt thereof with sodium polystyrene sulfonate, when a ready-to-suspend preparation is prepared.

With respect to the content, the method of addition, or the like, of each component in the use of the hydrophobic substance of the present invention, the explanations for the pharmaceutical composition of the present invention and its production method can be directly applied.

EXAMPLES

Mirabegron, which was used in the Examples or the like below, had been prepared in accordance with methods described in WO 99/20607 or WO 03/037881.

The present invention will now be further illustrated by, but is by no means limited to, the following Examples and Experimental Examples.

Example 1

(1) Preparation of Complex

To 11400 g of purified water, 2400 g of sodium polystyrene sulfonate (Amberlite (registered trademark) IRP69, The Dow Chemical Company), 1200 g of pulverized mirabegron, and 1639 g of dilute hydrochloric acid (Merck & Co., Inc.) were added, and the mixture was stirred to prepare a complex liquid. The reaction temperature was 50° C. The obtained complex liquid was spray-dried, and the complex was recovered as powder.

(2) Preparation of Granulated Product

A binder liquid was prepared by dissolving 168 g of hypromellose (TC-5R, Shin-Etsu Chemical Co., Ltd., Unless otherwise stated, the same compound was used in the following) in 1932 g of purified water. The binder liquid was used to granulate 1753 g of the complex of Example 1(1), 700 g of xanthan gum (Xantural 11K, CP Kelco), and 2251 g of mannitol (Pearlitol 50C, ROQUETTE, Unless otherwise stated, the same compound was used in the following). With the obtained granulated product, 56 g of magnesium stearate (Parteck (registered trademark) LUB MST, Merck & Co., Inc., Unless otherwise stated, the same compound was used in the following) was mixed to obtain a pharmaceutical composition.

Example 2

A binder liquid was prepared by dissolving 144 g of hypromellose in 1656 g of purified water. The binder liquid was used to granulate 1502.4 g of the complex, which had been prepared under the same conditions as those in Example 1(1), 600 g of xanthan gum (Xantural 11K, CP Kelco), 1735.2 g of mannitol, 360 g of acesulfame potassium (MC Food Specialties Inc., Unless otherwise stated, the same compound was used in the following), 14.4 g of simethicone (Dow Corning Toray Co., Ltd., Unless otherwise stated, the same compound was used in the following), 288 g of pulverized methyl parahydroxybenzoate (UENO FINE CHEMICALS INDUSTRY, LTD., Unless otherwise stated, the same compound was used in the following), and 108 g of pulverized ethyl parahydroxybenzoate (UENO FINE CHEMICALS INDUSTRY, LTD., Unless otherwise stated, the same compound was used in the following). With 990 g of the obtained granulated product, 10 g of magnesium stearate and 1 g of light anhydrous silicic acid (Sylysia (registered trademark), Fuji Silysia Chemical Ltd.) were mixed to obtain a pharmaceutical composition.

Example 3

A binder liquid was prepared by dissolving 14.4 g of hypromellose in 165.6 g of purified water. The binder liquid was used to granulate 150.24 g of the complex, which had been prepared under the same conditions as those in Example 1(1), 60 g of xanthan gum (Xantural 180, CP Kelco), 163.92 g of mannitol, 36 g of acesulfame potassium, 1.44 g of simethicone, 28.8 g of pulverized methyl parahydroxybenzoate, and 10.8 g of pulverized ethyl parahydroxybenzoate. With the obtained granulated product, 14.4 g of magnesium stearate was mixed to obtain a pharmaceutical composition.

Example 4

A binder liquid was prepared by dissolving 144 g of hypromellose in 1656 g of purified water. The binder liquid was used to granulate 1502.4 g of the complex, which had been prepared under the same conditions as those in Example 1(1), 600 g of xanthan gum (Xantural 11K, CP Kelco), 1730.4 g of mannitol, 360 g of acesulfame potassium, 14.4 g of simethicone, 288 g of pulverized methyl parahydroxybenzoate, and 108 g of pulverized ethyl parahydroxybenzoate. With the obtained granulated product, 48 g of magnesium stearate and 4.8 g of light anhydrous silicic acid were mixed to obtain a pharmaceutical composition.

Example 5

To 4560 g of purified water, 960 g of sodium polystyrene sulfonate (Amberlite IRP69, The Dow Chemical Company), 480 g of pulverized mirabegron, and 655.7 g of dilute hydrochloric acid (Merck & Co., Inc.) were added, and the mixture was stirred to prepare a complex liquid. The reaction temperature was 50° C. The obtained complex liquid was spray-dried together with 1730.4 g of mannitol, and was recovered as a mixture of the complex with mannitol.

A binder liquid was prepared by dissolving 144 g of hypromellose in 1656 g of purified water. The binder liquid was used to granulate the total amount of the mixture of the complex and mannitol, 150 g of xanthan gum (Xantural 11K, CP Kelco), 995.7 g of mannitol, 90 g of acesulfame potassium, 14.4 g of simethicone, 84 g of pulverized methyl parahydroxybenzoate, and 31.5 g of pulverized ethyl parahydroxybenzoate. With the obtained granulated product, 48 g of magnesium stearate and 9.6 g of light anhydrous silicic acid were mixed to obtain a pharmaceutical composition.

Example 6

A binder liquid was prepared by dissolving 144 g of hypromellose in 1656 g of purified water. The binder liquid was used to granulate 1502.4 g of the complex, which had been prepared under the same conditions as those in Example 1(1), 600 g of xanthan gum (Xantural 11K, CP Kelco), 1735.2 g of mannitol, 360 g of acesulfame potassium, 14.4 g of simethicone, 288 g of pulverized methyl parahydroxybenzoate, and 108 g of pulverized ethyl parahydroxybenzoate. With 100 g of the obtained granulated product, 0.1 g of light anhydrous silicic acid was mixed to obtain a mixture.

With 991 mg of the mixture, 10 mg of calcium stearate (Parteck (registered trademark) LUB CST, Merck & Co., Inc.) was mixed to obtain a pharmaceutical composition.

Example 7

With 991 mg of the mixture of Example 6, 10 mg of talc (Crown Talc, Matsumura Sangyo Co., Ltd.) was mixed, instead of calcium stearate, to obtain a pharmaceutical composition.

Example 8

With 991 mg of the mixture of Example 6, 10 mg of calcium carbonate (precipitated calcium carbonate, Kozakai Pharmaceutical Co., Ltd.) was mixed, instead of calcium stearate, to obtain a pharmaceutical composition.

Example 9

With 991 mg of the mixture of Example 6, 10 mg of stearic acid (Japanese pharmacopoeia, stearic acid, NOF CORPORATION) was mixed, instead of calcium stearate, to obtain a pharmaceutical composition.

TABLE 1

| <Formulation> | | | |
|---|---|---|---|
| | Example 1 (mg/bottle) | Example 2 (mg/bottle) | Example 3 (mg/bottle) |
| Mirabegron | 400 | 400 | 400 |
| Sodium polystyrene sulfonate | 800 | 800 | 800 |
| Dilute hydrochloric acid [1] | 52 | 52 | 52 |
| Mannitol | 1608 | 1446 | 1366 |
| Xanthan gum | 500 | 500 | 500 |
| Hypromellose | 120 | 120 | 120 |
| Magnesium stearate | 40 | 40 | 120 |
| Acesulfame potassium | — | 300 | 300 |
| Methyl parahydroxybenzoate | — | 240 | 240 |
| Ethyl parahydroxybenzoate | — | 90 | 90 |
| Simethicone | — | 12 | 12 |
| Light anhydrous silicic acid | — | 4 | — |
| Total amount | 3520 | 4004 | 4000 |

[1] Amount corresponding to hydrochloric acid in 10% dilute hydrochloric acid

TABLE 2

| | Example 4 (mg/bottle) | Example 5 (mg/bottle) |
|---|---|---|
| Mirabegron | 400 | 400 |
| Sodium polystyrene sulfonate | 800 | 800 |
| Dilute hydrochloric acid [2] | 52 | 52 |
| Mannitol | 1442 | 2271.75 |
| Xanthan gum | 500 | 125 |
| Hypromellose | 120 | 120 |
| Magnesium stearate | 40 | 40 |
| Acesulfame potassium | 300 | 75 |
| Methyl parahydroxybenzoate | 240 | 70 |
| Ethyl parahydroxybenzoate | 90 | 26.25 |
| Simethicone | 12 | 12 |
| Light anhydrous silicic acid | 4 | 8 |
| Total amount | 4000 | 4000 |

[2] Amount corresponding to hydrochloric acid in 10% dilute hydrochloric acid

TABLE 3

|  | Example 6 (mg/bottle) | Example 7 (mg/bottle) | Example 8 (mg/bottle) | Example 9 (mg/bottle) |
|---|---|---|---|---|
| Mirabegron | 100 | 100 | 100 | 100 |
| Sodium polystyrene sulfonate | 200 | 200 | 200 | 200 |
| Dilute hydrochloric acid [3] | 13 | 13 | 13 | 13 |
| Mannitol | 361.5 | 361.5 | 361.5 | 361.5 |
| Xanthan gum | 125 | 125 | 125 | 125 |
| Acesulfame potassium | 75 | 75 | 75 | 75 |
| Methyl parahydroxybenzoate | 60 | 60 | 60 | 60 |
| Ethyl parahydroxybenzoate | 22.5 | 22.5 | 22.5 | 22.5 |
| Hypromellose | 30 | 30 | 30 | 30 |
| Simethicone | 3 | 3 | 3 | 3 |
| Calcium stearate | 10 | — | — | — |
| Talc | — | 10 | — | — |
| Calcium carbonate | — | — | 10 | — |
| Stearic acid | — | — | — | 10 |
| Light anhydrous silicic acid | 1 | 1 | 1 | 1 |
| Total amount | 1001 | 1001 | 1001 | 1001 |

[3] Amount corresponding to hydrochloric acid in 10% dilute hydrochloric acid

Comparative Example 1

(1) Preparation of Complex

A complex liquid was prepared by dissolving 100 g of pulverized mirabegron in 10 L of 0.1 N hydrochloric acid, and adding thereto 620 mL of 1 N aqueous sodium hydroxide solution and 200 g of polacrillin potassium (Amberlite IRP88, The Dow Chemical Company). The obtained complex liquid was dried at 70° C., and sieved at 250 µm to recover the complex as powder.

(2) Preparation of Coated Product

A coating liquid was prepared by stirring 99 g of triethyl citrate (Merck & Co., Inc.) in 1651 g of an ethylcellulose aqueous dispersion (Aquacoat ECD, FMC Corporation). With respect to 270 g of the complex, which had been prepared under the same conditions as those in Comparative Example 1(1), 906 g of the coating liquid was sprayed in a fluidized bed granulator, and the granulated product was dried at 70° C. to obtain a pharmaceutical composition.

Example 10

A complex liquid was prepared by adding 960 g of sodium polystyrene sulfonate (Purolite (registered trademark) C100MRNS, Purolite Ltd.), 480 g of pulverized mirabegron, and 655.7 g of dilute hydrochloric acid (Merck & Co., Inc.) to 4560 g of purified water, and stirring the mixture. The reaction temperature was 50° C. The obtained complex liquid was spray-dried together with 1730.4 g of mannitol to recover the complex as powder.

A binder liquid was prepared by dissolving 144 g of hypromellose in 1656 g of purified water. The binder liquid was used to granulate the total amount of the mixture of the complex and mannitol, 600 g of xanthan gum (Xantural 11K, CP Kelco), 360 g of acesulfame potassium, 14.4 g of simethicone, 288 g of pulverized methyl parahydroxybenzoate, and 108 g of pulverized ethyl parahydroxybenzoate. With the obtained granulated product, 48 g of magnesium stearate and 4.8 g of light anhydrous silicic acid were mixed to obtain a pharmaceutical composition.

Example 11

A complex liquid was prepared by adding 960 g of sodium polystyrene sulfonate (Purolite (registered trademark) NaResNS, Purolite Ltd.), 480 g of pulverized mirabegron, and 655.7 g of dilute hydrochloric acid (Merck & Co., Inc.) to 4560 g of purified water, and stirring the mixture. The reaction temperature was 50° C. The obtained complex liquid was spray-dried together with 1730.4 g of mannitol to recover the complex as powder.

A binder liquid was prepared by dissolving 144 g of hypromellose in 1656 g of purified water. The binder liquid was used to granulate the total amount of the mixture of the complex and mannitol, 600 g of xanthan gum (Xantural 11K, CP Kelco), 360 g of acesulfame potassium, 14.4 g of simethicone, 288 g of pulverized methyl parahydroxybenzoate, and 108 g of pulverized ethyl parahydroxybenzoate. With the obtained granulated product, 48 g of magnesium stearate and 4.8 g of light anhydrous silicic acid were mixed to obtain a pharmaceutical composition.

TABLE 4

|  | Comparative Example 1 (mg/bottle) | Example 10 (mg/bottle) | Example 11 (mg/bottle) |
|---|---|---|---|
| Mirabegron | 50 | 400 | 400 |
| Polacrillin potassium | 100 | — | — |
| Sodium polystyrene sulfonate | — | 800 | 800 |
| 0.1N hydrochloric acid [4] | (18.2) | — | — |
| Dilute hydrochloric acid [4] | — | 52 | 52 |
| 1N aqueous sodium hydroxide solution [5] | (12.4) | — | — |
| (Sodium chloride) [6] | 18.1 | — | — |
| Mannitol | (110.31) [8] | 1442 | 1442 |
| Xanthan gum | (62.5) [8] | 500 | 500 |
| Hypromellose | (20.79) [8] | 120 | 120 |
| Magnesium stearate | (7) [8] | 40 | 40 |
| Ethylcellulose [7] | 131.6 | — | — |
| Triethyl citrate | 26.3 | — | — |
| Acesulfame potassium | — | 300 | 300 |
| Methyl parahydroxybenzoate | — | 240 | 240 |
| Ethyl parahydroxybenzoate | — | 90 | 90 |
| Simethicone | — | 12 | 12 |
| Light anhydrous silicic acid | — | 4 | 4 |
| Total amount | 326.1 [9] | 4000 | 4000 |

[4] Amount corresponding to hydrochloric acid in 0.1N hydrochloric acid or 10% dilute hydrochloric acid
[5] Amount corresponding to sodium hydroxide in 1N aqueous sodium hydroxide solution
[6] Amount corresponding to sodium chloride generated from hydrochloric acid and sodium hydroxide
[7] Amount corresponding to ethylcellulose in ethylcellulose aqueous dispersion
[8] Amount dissolved in water for suspension, when used
[9] Theoretical amount of solids in pharmaceutical composition Experimental Example 1

Dissolution Test

A suspension (suspension liquid) in which the pharmaceutical composition of Example 1 was suspended in 200 mL of water; and a suspension in which the solid component of Comparative Example 1 was suspended in 25 mL of water containing mannitol, xanthan gum, hypromellose, and magnesium stearate at the amounts as shown in Table 4; were prepared. Separately, 25 mL of each suspension (containing 50 mg of mirabegron) was added to 875 mL of 0.1 N hydrochloric acid, as a test liquid, and a dissolution test was carried out in accordance with a paddle method at a paddle rotation speed of 200 rpm. The dissolution rate was calculated by measuring the amount of the drug dissoluted after predetermined periods of time by an ultraviolet-visible absorption spectroscopy (UV-VIS method). The results are shown in FIG. 1. The suspension of the present invention inhibited the dissolution of mirabegron under acidic conditions, in comparison to the suspension of Comparative Example 1.

Experimental Example 2

Dissolution Test

To 900 mL of a phosphate buffer solution, pH 6.8 (US pharmacopeia), 4 mL (containing 8 mg of mirabegron) of each suspension (suspension liquid), which had been prepared by separately suspending the pharmaceutical compositions of Examples 4, 10, and 11 in 200 mL of water, was separately added, and a dissolution test was carried out in accordance with a paddle method at a paddle rotation speed of 50 rpm. With respect to the same suspensions (suspension liquids), 25 mL (containing 50 mg of mirabegron) of each suspension was separately added to 875 mL of each test liquid (i.e., water, 0.1 N hydrochloric acid, an acetate buffer solution, pH 4.5, or a phosphate buffer solution, pH 6.8 (European pharmacopoeia)), and a dissolution test was carried out in accordance with a paddle method at a paddle rotation speed of 50 rpm. The dissolution rate was calculated by measuring the samples by a high performance liquid chromatography (HPLC method). The results are shown in FIGS. 2 to 6.

The suspensions of Examples 4, 10, and 11 all had similar dissolution properties. In particular, the suspension of Example 4 had a higher inhibitory effect on dissolution, in the phosphate buffer solution, pH 6.8 (US pharmacopeia).

Sodium polystyrene sulfonate has different swelling rates in water, for each product. It is considered that the suspension of Example 4 inhibited the dissolution properties of mirabegron more strongly, by using sodium polystyrene sulfonate (Amberlite (registered trademark) IRP69) having a low swelling rate.

The concentration of mirabegron was determined under the following conditions. As a HPLC column, Develosil ODS-HG-3 (particle size: 3 µm, 4.6 mm (inner diameter)×15 cm, manufactured by Nomura Chemical Co., Ltd.) was used. As a mobile phase maintained at 40° C., pH 2.0 perchlorate buffer/acetonitrile (3:1) was used. Sample solutions were prepared and used by passing samples for the dissolution test through a filter. The flow rate was adjusted so that the retention time of mirabegron was about 5 minutes. The measurement was carried out using an ultraviolet absorption spectrophotometer (wavelength: 225 nm), the percentage was calculated from the peak area ratio of mirabegron with respect to a standard substance.

Experimental Example 3

PK Test in Dogs

To six male beagle dogs each, 25 mL (corresponding to 50 mg of mirabegron) of each suspension of Example 1 or Comparative Example 1, which had been prepared in a similar manner to that of Experimental Example 1, was orally administered in a fasted state. After the administration, blood was periodically collected, and the concentration of mirabegron in plasma obtained by centrifugation was measured. The dogs were made to fast 16 hours or more ahead of the scheduled administration time. Further, the dogs were subjected to pentagastrin treatment (intramuscular administration in the buttocks; 30 minutes before administration, and 30 and 90 minutes after administration) to control the intragastric pH to acidic, and the test was carried out.

The time to reach the maximum plasma concentration of an unchanged form (Tmax) of the suspensions of Example 1 and Comparative Example 1 is shown in Table 5. It was found that Tmax of the suspension of Example 1 significantly increased in comparison to the suspension of Comparative Example 1.

TABLE 5

| | Comparative Example 1 | Example 1 |
|---|---|---|
| Tmax (hours) | 1.5 ± 0.77 | 3.67 ± 3.44 |

(Mean ± SD)

Experimental Example 4

To a bottle, 1001 mg of the pharmaceutical composition of Example 2 and 50 mL of purified water were added, and the bottle was allowed to stand for 2 minutes, and was shaken to prepare a suspension (shaking conditions: 20 reciprocal shaking for 10 seconds at a distance of 20 cm). The suspension was, sieved, and the number of remaining undissolved lumps was counted. The results are shown in Table 6.

TABLE 6

| | Example 2 |
|---|---|
| >2800 µm | 0 |

Experimental Example 5

To a bottle, the pharmaceutical composition of Example 3 and 200 mL of purified water were added, and the bottle was shaken to prepare a suspension (shaking conditions: 50 reciprocal shaking for 10 seconds at a distance of 20 cm, and 100 reciprocal shaking for 50 seconds). The bottle was allowed to stand for 10 minutes, re-shaken under the same conditions, and allowed to stand for 3 minutes. The suspension was sieved, and the number of remaining undissolved lumps was counted. The results are shown in Table 7.

TABLE 7

| | Example 3 |
|---|---|
| >2800 µm | 0 |

Experimental Example 6

Sedimentation Test

Each of the pharmaceutical compositions of Examples 1 to 3 and 200 mL of purified water were added to bottles, and the bottles were shaken under the same conditions as those of Experimental Example 5 to prepare suspensions. After the shaking, the bottles were allowed to stand, and it was visually confirmed whether the complex was sedimented.

Even after the bottle was allowed to stand at room temperature for 12 hours, the sedimentation of the complex was not observed.

Experimental Example 7

Viscosity Test

Each of the pharmaceutical compositions of Examples 1 to 3 and 200 mL of purified water were added to bottles, and the bottles were shaken under the same conditions as those of Experimental Example 5 to prepare suspensions. The viscosity was measured at 25° C. and at a paddle rotation speed of 100 rpm, using a rotational viscometer (Brookfield digital viscometer, Model: RVDV-II+PRO). The results are shown in Table 8. The spindle was appropriately selected depending on the viscosity.

TABLE 8

|  | Spindle | Viscosity (mPa · s) |
|---|---|---|
| Example 1 | RV-3 | 129 |
| Example 2 | RV-3 | 109 |
| Example 3 | RV-3 | 110 |

Experimental Example 8

Each of the pharmaceutical compositions of Examples 5 to 9 and 50 mL of purified water were added to bottles. The bottles were allowed to stand for 2 minutes, and shaken to prepare suspensions (shaking conditions: 20 reciprocal shaking for 10 seconds at a distance of 20 cm). The suspensions were sieved, and the number of remaining undissolved lumps was counted. The results are shown in Table 9.

TABLE 9

|  | >2800 μm | 1400~2800 μm |
|---|---|---|
| Example 5 | 0 | 0 |
| Example 6 | 0 | 0 |
| Example 7 | 1 | 4 |
| Example 8 | 4 | 7 |
| Example 9 | 1 | 6 |

Experimental Example 9

The pharmaceutical compositions of Examples 2, 6, 8, and 9 were compression-molded to prepare cylindrical tablets (diameter: 7 mm, thickness: 2.8 mm). On the surface of each tablet, 2 μL of a water droplet was dropped, and the contact angle was measured using a contact angle measuring apparatus (DM-501, Kyowa Interface Science Co., Ltd.) after 100 msec. from the drop of the droplet on the surface of the tablet at room temperature. The results are shown in Table 10.

TABLE 10

|  | Average contact angle (°) | Standard deviation |
|---|---|---|
| Example 2 | 91.4 | 1.5 |
| Example 6 | 92.6 | 2.1 |

TABLE 10-continued

|  | Average contact angle (°) | Standard deviation |
|---|---|---|
| Example 8 | 67.5 | 1.8 |
| Example 9 | 72.4 | 2.9 |

INDUSTRIAL APPLICABILITY

According to the pharmaceutical composition of the present invention, a modified release liquid (suspension) containing mirabegron can be provided, and by rendering mirabegron as a modified release liquid (suspension), it can be taken for a patient who needs dose adjustment, such as a child, and drug dosing compliance is improved. According to the pharmaceutical composition of the present invention, the pharmaceutical composition can be dispersed with simple shaking, without using a special instrument when suspended at the time of use, and the generation of undissolved lumps can be inhibited.

Although the present invention has been described with reference to specific embodiments, various changes and modifications obvious to those skilled in the art are possible without departing from the scope of the appended claims.

The invention claimed is:

1. A pharmaceutical composition comprising a complex of mirabegron or a pharmaceutically acceptable salt thereof with sodium polystyrene sulfonate, a thickener, and a hydrophobic substance, wherein the hydrophobic substance is magnesium stearate and/or calcium stearate.

2. The pharmaceutical composition according to claim 1, wherein the content of the hydrophobic substance is 0.5% by weight to 35% by weight with respect to the weight of the thickener.

3. The pharmaceutical composition according to claim 1 or 2, wherein the thickener is one member or two or more members selected from the group consisting of xanthan gum, guar gum, locust bean gum, gellan gum, carboxymethyl cellulose sodium, gelatin, hydroxyethyl cellulose, hydroxypropyl cellulose, carrageenan, methylcellulose, sodium alginate, hypromellose, and polyvinyl alcohol.

4. The pharmaceutical composition according to claims 1 or 2 wherein the thickener is xanthan gum.

5. The pharmaceutical composition according to claim 1 or 2, wherein the content of the thickener is 1% by weight to 70% by weight with respect to the weight of the pharmaceutical composition.

6. The pharmaceutical composition according to claim 1 or 2, wherein the pharmaceutical composition is a ready-to-suspend pharmaceutical composition.

7. The pharmaceutical composition according to claim 1 or 2, wherein the pharmaceutical composition is a pharmaceutical composition for oral administration.

8. The pharmaceutical composition according to claim 1 or 2, wherein the pharmaceutical composition is a pharmaceutical composition for treating one member or two or more members selected from the group consisting of urinary urgency, urinary frequency, urge urinary incontinence, and neuropathic detrusor overactivity, which are associated with overactive bladder.

9. A method for modifying the release of mirabegron, the method comprising:

administering a composition comprising a complex with mirabegron or a pharmaceutically acceptable salt thereof and sodium polystyrene, a thickener and a hydrophobic substance, wherein the hydrophobic substance is magnesium stearate and/or calcium stearate.

\* \* \* \* \*